US011450435B2

(12) United States Patent
Junio

(10) Patent No.: US 11,450,435 B2
(45) Date of Patent: Sep. 20, 2022

(54) SPINAL STENOSIS DETECTION AND GENERATION OF SPINAL DECOMPRESSION PLAN

(71) Applicant: MAZOR ROBOTICS LTD., Caesarea (IL)

(72) Inventor: Dany Junio, Tel Aviv-Jaffa (IL)

(73) Assignee: MAZOR ROBOTICS LTD., Caesarea (IL)

( * ) Notice: Subject to any disclaimer, the term of this patent is extended or adjusted under 35 U.S.C. 154(b) by 137 days.

(21) Appl. No.: 16/842,380

(22) Filed: Apr. 7, 2020

(65) Prior Publication Data
US 2021/0313062 A1 Oct. 7, 2021

(51) Int. Cl.
*G16H 30/40* (2018.01)
*G16H 50/20* (2018.01)
(Continued)

(52) U.S. Cl.
CPC ........... *G16H 50/20* (2018.01); *A61B 5/4566* (2013.01); *A61B 5/7264* (2013.01); *G06T 7/0014* (2013.01); *G16H 20/30* (2018.01); *G16H 30/20* (2018.01); *G16H 30/40* (2018.01); *G16H 50/50* (2018.01); *G16H 50/70* (2018.01); *G06T 2207/30012* (2013.01)

(58) Field of Classification Search
CPC ........ G16H 50/20; G16H 20/30; G16H 30/20; G16H 30/40; G16H 50/50; G16H 50/70; A61B 5/4566; A61B 5/7264; A61B 34/10; G06T 7/0014; G06T 2207/30012; G06T 7/62; G06T 2207/10072; G06T 2207/20081; G06T 2207/20084; G06T 7/0012

USPC ........................................................ 705/2–3
See application file for complete search history.

(56) References Cited

U.S. PATENT DOCUMENTS 5,270,654 A * 12/1993 Feinberg ............ G01R 33/5615
324/307
6,608,916 B1 8/2003 Wei et al.
(Continued)

FOREIGN PATENT DOCUMENTS

CN 108492874 9/2018
CN 109934824 6/2019
(Continued)

OTHER PUBLICATIONS

Al-Kafri, Boundary Delineation of MRI Images for Lumbar Spinal Stenosis Detection Through Semantic Segmentation Using Deep Neural Networks, 2019, IEEE Access, vol. 7, pp. 43487-43501 (Year: 2019).*
(Continued)

*Primary Examiner* — Joshua B Blanchette
*Assistant Examiner* — Tran N Nguyen
(74) *Attorney, Agent, or Firm* — Sheridan Ross P.C.

(57) ABSTRACT

A method and system for detecting spinal stenosis is provided. The method may receive image data corresponding to a spine region of a patient. The method may also identify a spinal cord in the image data. The method may determine at least one compression of the spinal cord and may mark an anatomical element proximate to a location of the determined at least one compression to yield at least one marking. The method may generate a decompression plan based on the at least one marking.

20 Claims, 8 Drawing Sheets

(51) Int. Cl.
    *G16H 30/20*     (2018.01)
    *G16H 50/50*     (2018.01)
    *G16H 50/70*     (2018.01)
    *A61B 5/00*     (2006.01)
    *G06T 7/00*     (2017.01)
    *G16H 20/30*     (2018.01)
    *G16H 20/00*     (2018.01)

(56) References Cited

U.S. PATENT DOCUMENTS

| | | | |
|---|---|---|---|
| 6,711,432 | B1 | 3/2004 | Krause et al. |
| 6,979,294 | B1* | 12/2005 | Selzer .............. A61B 8/463 |
| | | | 600/450 |
| 7,374,536 | B1* | 5/2008 | Taylor .............. A61B 5/00 |
| | | | 600/300 |
| 8,014,575 | B2* | 9/2011 | Weiss .............. A61B 5/0036 |
| | | | 382/128 |
| 9,020,235 | B2* | 4/2015 | Krishnan .............. A61B 6/469 |
| | | | 382/132 |
| 2006/0110017 | A1* | 5/2006 | Tsai .............. G06T 7/0012 |
| | | | 382/128 |
| 2007/0036416 | A1 | 2/2007 | Tsai et al. |
| 2007/0173744 | A1* | 7/2007 | Lai .............. G06T 7/136 |
| | | | 600/587 |
| 2007/0223799 | A1 | 9/2007 | Weiss |
| 2009/0202122 | A1 | 8/2009 | Wang |
| 2009/0240137 | A1 | 9/2009 | Rosa |
| 2010/0086185 | A1 | 4/2010 | Weiss |
| 2012/0143090 | A1 | 6/2012 | Hay et al. |
| 2012/0172700 | A1 | 7/2012 | Krishman et al. |
| 2013/0191154 | A1 | 7/2013 | Dobkin et al. |
| 2014/0064583 | A1 | 3/2014 | Wang et al. |
| 2014/0081659 | A1* | 3/2014 | Nawana .............. G16H 50/50 |
| | | | 705/3 |
| 2015/0080729 | A1* | 3/2015 | Miyachi .............. A61B 8/0891 |
| | | | 600/443 |
| 2015/0173701 | A1 | 6/2015 | Major et al. |
| 2015/0182288 | A1 | 7/2015 | Greenwald et al. |
| 2015/0248593 | A1 | 9/2015 | Nakashima et al. |
| 2015/0254839 | A1 | 9/2015 | Yoo |
| 2015/0356729 | A1 | 12/2015 | Hladuvka et al. |
| 2016/0267655 | A1 | 9/2016 | Akahori |
| 2016/0364862 | A1 | 12/2016 | Reicher et al. |
| 2017/0252107 | A1 | 9/2017 | Turner et al. |
| 2019/0021677 | A1 | 1/2019 | Grbic et al. |
| 2020/0038111 | A1* | 2/2020 | Turner .............. G16H 50/50 |
| 2020/0315708 | A1 | 10/2020 | Mosnier et al. |

FOREIGN PATENT DOCUMENTS

| | | |
|---|---|---|
| JP | 2010-029482 | 2/2010 |
| JP | 6582171 | 9/2019 |
| KR | 10-2014-0064583 | 5/2014 |
| KR | 102062539 | 1/2020 |
| WO | WO 2019/012520 | 6/2012 |

OTHER PUBLICATIONS

Ito, Step-by-Step Sublaminar Approach With a Newly-Designed Spinal Endoscope for Unilateral-Approach Bilateral Decompression in Spinal Stenosis, 2019, Neurospine 16(1):41-51 (Year: 2019).*
Ulbrich, Normative MR cervical spinal canal dimensions, 2013, Radiology, Apr. 2014; 271(1):172-82. doi: 10.1148/radiol. 13120370. Epub Dec. 12, 2013 PMID: 24475792. (Year: 2013).*
Lee, The anatomy of the thoracic spinal canal investigated with magnetic resonance imaging (MRI), 2007 Acta Anaesthesiol Belg.; 58(3):163-7 (Year: 2007).*
Maher, Lateral exit-zone stenosis and lumbar radiculopathy, 1999, J Neurosurg (Spine 1) 90:52-58 (Year: 1999).*
Koh, Automatic spinal canal detection in lumbar MR images in the sagittal view using dynamic programming, 2014, Computerized Medical Imaging and Graphics, vol. 38, Issue 7, pp. 569-579 (Year: 2014) (Year: 2014).*
Morishita, Cervical spinal canal stenosis: the differences between stenosis at the lower cervical and multiple segment levels, 2011, International Orthopaedics (SICOT) 35, 1517-1522 (Year: 2011) (Year: 2011).*
U.S. Appl. No. 16/845,788, filed Apr. 10, 2020, Benson.
Steiner et al., "Patient-Specific In Silico Models Can Quantify Primary Implant Stability in Elderly Human Bone," Journal of Orthopaedic Research, vol. 36, Mar. 2018, pp. 954-962.
Al Kafri et al., "Segmentation of Lumbar Spine MRI Images for Stenosis Detection Using Patch-Based Pixel Classification Neural Network," 2018 IEEE Congress on Evolutionary Computation, Jul. 2018, 8 pages.
Al Kafri, "Boundary Delineation of MRI Images for Lumbar Spinal Stenosis Detection through Semantic Segmentation Using Deep Neural Networks," IEEE Access, vol. 7, Apr. 1, 2019, pp. 433487-443501.
Chen et al., "Automatic Localization and Identification of Vertebrae in Spine CT via a Joint Learning Model with Deep Neural Networks," International Conference on Medical Image Computing and Computer-Assisted Intervention, Nov. 2015, pp. 512-522. Abstract only.
Gawel et al., "Automatic Spine Tissue Segmentation from MRI Data Based on Cascade of Boosted Classifiers and Active Appearance Model," BioMed Research International, vol. 2018, No. 7952946, Apr. 2018, 13 pages.
Kim et al., "Automatic detection and segmentation of lumbar vertebra from X-ray images for compression fracture evaluation," arXiv ePrint, vol. 1904.07624v1, Apr. 16, 2019, 18 pages.
Koompairojn et al., "Computer-Aided Diagnosis of Lumbar Stenosis Conditions," Proceedings of SPIE—The International Society for Optical Engineering, vol. 7624, Mar. 2010, 12 pages.
Lu et al., Deep Spine: Automated Lumbar Vertebral Segmentation, Disc-Level Designation, and Spinal Stenosis Grading Using Deep Learning, Proceedings of Machine Learning Research, vol. 85, Jul. 2018, 16 pages.
Neubert et al., "Automated detection, 3D segmentation and analysis of high resolution spine MR images using statistical shape models," Physics in Medicine & Biology, vol. 57, No. 24, Dec. 2012, pp. 7357-8376.
Qadri et al., "Automatic Deep Feature Learning via Patch-Based Deep Belief Network for Vertebrae Segmentation in CT Images," Applied Sciences, vol. 9, No. 69, 2019, 17 pages.
Suzani et al., "Deep Learning for Automatic Localization, Identification, and Segmentation of Vertebral Bodies in Volumetric MR Images," SPIE Medical Imaging 2015: Image-Guided Procedures, Robotic Interventions, and Modeling, vol. 9415-15, Feb. 2015, 7 pages.
Wang et al., Automatic Segmentation of Spinal Canals in CT Images via Iterative Topology Refinement, IEEE Transactions on Medical Imaging, vol. 34, No. 8, Aug. 2015, pp. 1694-1704.
Brusko et al. "Preoperative SPECT imaging as a tool for surgical planning in patients with axial neck and back pain," Journal of Neurosurgery, 2019, vol. 47, No. 6, article E19, 5 pages.
Official Action for U.S. Appl. No. 16/845,788, dated Dec. 24, 2021 13 pages.

* cited by examiner

SPINAL STENOSIS DETECTION AND GENERATION OF SPINAL DECOMPRESSION PLAN

FIELD

The present technology is related generally to spinal stenosis treatment and, more particularly, to spinal stenosis detection and generation of a spinal decompression plan based on image data.

BACKGROUND

Lumbar spinal stenosis, or compression of the spinal cord, is one of the largest contributors to spinal procedures in patients over 65. Spinal decompression procedures for relieving a spinal compression are delicate, time consuming, and high-risk tasks. Diagnosis of spinal stenosis is typically accomplished using a combination of patient imaging, patient verbal inputs, and physical examination of the patient. Once diagnosed, spinal stenosis may be treated with non-invasive means such as massages, chiropractic treatments, and/or acupuncture, and/or with invasive procedures including laminectomy, laminotomy, discectomy, and so forth. Due to the risk of removing bone or otherwise operating in a section of the spine where the nerves and bone are compressed together, accuracy is critical and significant concentration by the operating surgeon(s) is required. The physical work required during the procedure can also be intensive.

Conventional methods for planning and performing a spinal decompression procedure rely on a surgeon's prior experience, knowledge, and judgment. Such conventional methods are time consuming, complex, and may not be recorded for future reference or use. Surgical decompression plans often remain in the surgeon's head.

SUMMARY

Embodiments of the present disclosure advantageously provide objective approaches to detecting and planning a spinal decompression procedure, which reduce dependence on the treating physician's prior experience, knowledge, and judgment. Embodiments of the present disclosure may also beneficially reduce the time and costs involved in, increase the safety of, and improve the outcomes of spinal decompression procedures.

The present disclosure provides exemplary methods and systems for generating an optimized decompression plan by determining, from image data, at least one compression on a spinal cord and providing at least one marking of a corresponding anatomical element proximate to a location of the at least one compression.

A method for detecting spinal stenosis according to one embodiment of the present disclosure comprises: receiving image data corresponding to a spine region of a patient; identifying a spinal cord in the image data; determining at least one compression of the spinal cord; and marking an anatomical element proximate to a location of the determined at least one compression to yield at least one marking.

The method may further comprise classifying a type for each of the at least one compression. The method may further comprise generating a decompression plan based on the at least one marking. Generating the decompression plan may comprise: calculating an amount of bone to remove based on the at least one marking. Generating the decompression plan may comprise calculating a score for each of a plurality of potential decompression plans. Generating the decompression plan may comprise generating a visualization of a predicted appearance of the spine region after the decompression plan has been performed. At least one of the steps of identifying the spinal cord in the image data, determining the at least one compression of the spinal cord, marking the anatomical element, classifying the type, and calculating the amount of bone to remove may use at least one of machine learning, deep learning, and artificial intelligence. At least one of identifying the spinal cord in the image data, determining the at least one compression in the spinal cord, and marking the anatomical element may use feature-based identification.

Determining the at least one compression of the spinal cord may include comparing a first characteristic in the image data with a second characteristic in the image data to determine the at least one compression. Determining the at least one compression of the spinal cord may include comparing a characteristic in the image data with a predetermined threshold and determining that the characteristic meets the predetermined threshold. Generating the decompression plan may include selecting at least one of a full laminectomy, a partial laminectomy, a full laminotomy, a partial laminotomy, a full foraminotomy, and a partial foraminotomy. Generating the decompression plan may be based at least in part on historical decompression surgery data comprising information regarding a historical patient having a historical characteristic similar to a characteristic of the patient.

Another method for detecting spinal stenosis according to one embodiment of the present disclosure comprises: receiving image data corresponding to a spine region; identifying, in the image data, a spinal cord and at least one nerve exit proximal to the spinal cord; identifying a first side of the spinal cord and a second side of the spinal cord; determining, at each of a plurality of locations along the spinal cord in the superior-inferior (S-I) direction, a width between the first side and the second side of the spinal cord; calculating a change in the determined width for each adjacent pair of the plurality of locations; identifying a compression of the spinal cord when the calculated change in the determined width meets a threshold change; and classifying a type and a location for each of the at least one compression.

The method may further comprise generating a cross-section of the spinal cord along a plane extending in the S-I direction. The method may further comprise generating a plurality of graphs, each corresponding to one of the plurality of locations, based on a measurement orthogonal to the cross-section of the spinal cord, wherein each of the plurality of graphs depicts a first peak and a second peak, the first peak having a height corresponding to a maximum magnitude of a first gradient corresponding to the first side, the second peak having a height corresponding to a maximum magnitude of a second gradient corresponding to the second side, and a distance between the first peak and the second peak corresponding to the width.

Determining the change in the determined width may be based on comparison of the graphs corresponding to an adjacent pair of the plurality of locations. The method may further comprise annotating the image data based on a classification of the at least one compression. The method may further comprise marking, in the image data, an anatomical element proximate to a location of the determined at least one compression to yield at least one marking. The method may further comprise generating a decompression plan based on at least one of the classification for each of the at least one compression and the at least one marking.

A system for detecting spinal stenosis according to one embodiment of the present disclosure comprises: an imaging device imaging a spine region to yield image data; a processor; and a memory storing instructions for execution by the processor that, when executed, cause the processor to: receive the image data; identify a spinal cord in the image data; determine at least one compression in the spinal cord; mark, in the image data, an anatomical element proximate to a location of the determined at least one compression to yield at least one marking; and generate a decompression plan based on the at least one marking.

The memory may further include instructions that, when executed, cause the processor to: classify a type for each of the at least one compression. The memory may further include instructions that, when executed, cause the processor to: calculate an area for bone removal on the spinal cord based on the at least one marking for the decompression plan. The memory may further include instructions that, when executed, cause the processor to: select at least one of a full laminectomy, a partial laminectomy, a full laminotomy, a partial laminotomy, a full foraminotomy, and a partial foraminotomy for the decompression plan.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
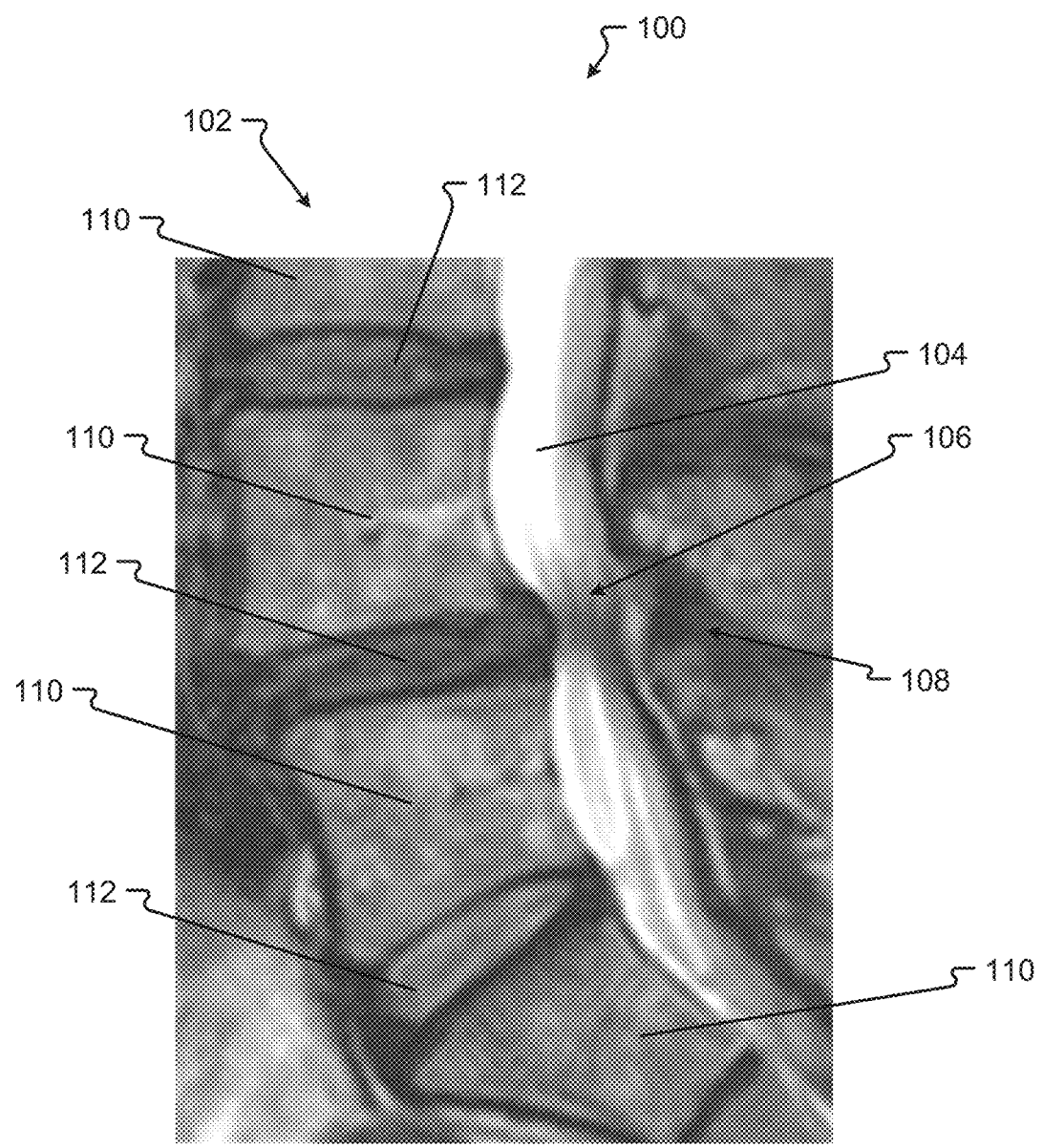
FIG. 1 is a side cross-section view that illustrates a spine region.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Figure 2B:
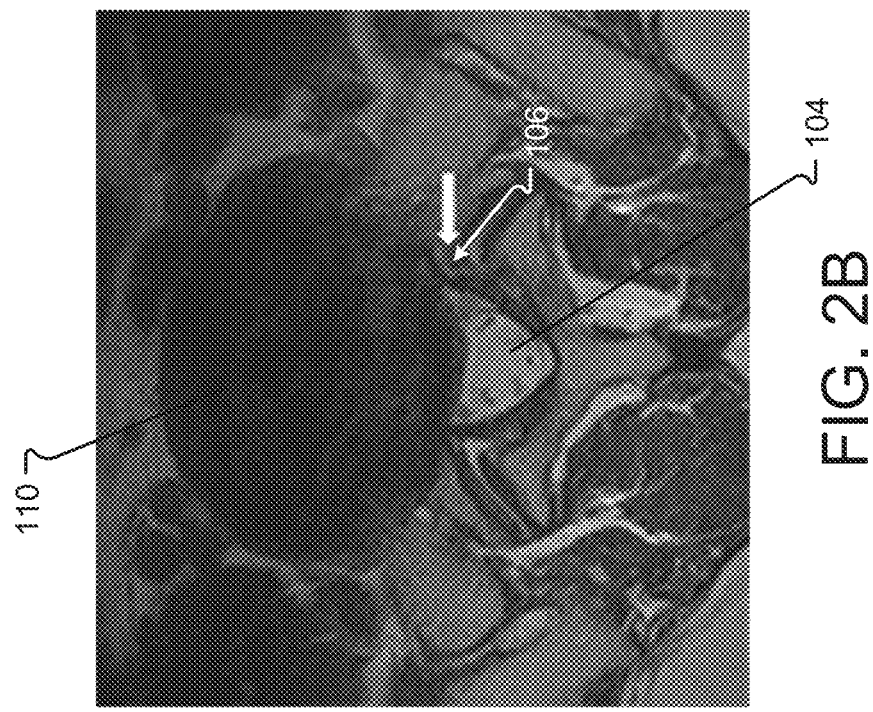
FIG. 2B is a top cross-section view that illustrates the spine region shown in FIG. 2B.
Figure 2A:
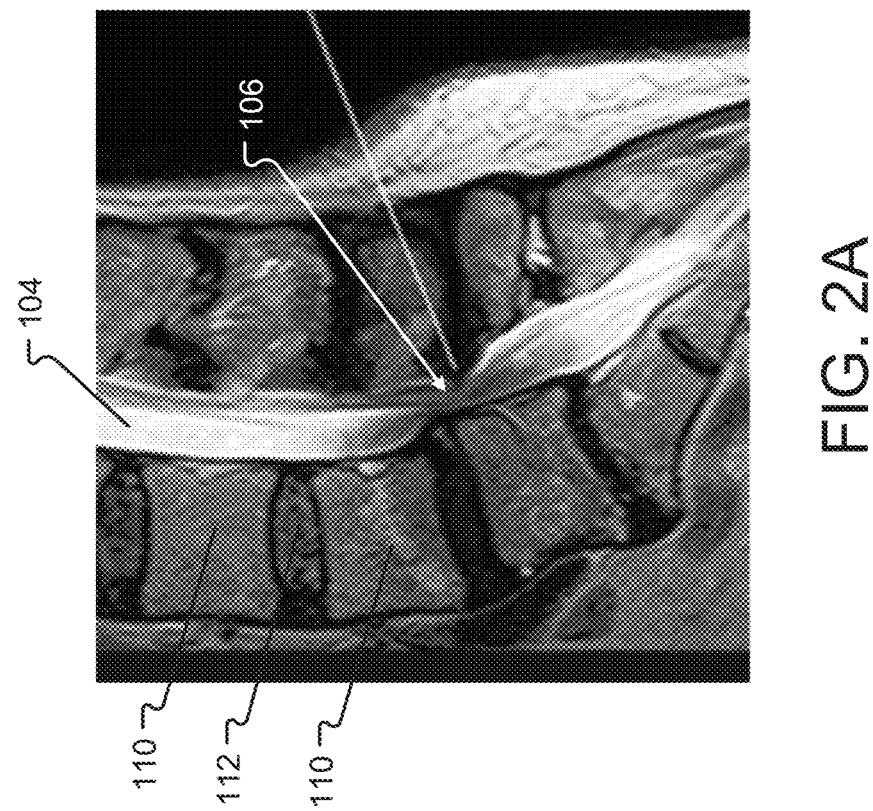
FIG. 2A is a side cross-section view that illustrates another spine region with a severe spinal stenosis.

Turning to the Figures, FIGS. 1, 2A, and 2B illustrate image data 100 showing a first side cross-section view, a second side cross-section view, and a top cross-section view, respectively, of a spine region 102. The image data 100 may be obtained from, for example, an MRI scan, a CT scan, or another 3D image. The spine region 102 includes a spinal cord 104, a plurality of vertebrae 110, and at least one nerve exit 108 extending from the spinal cord 104.

At least one compression 106 of the spinal cord 104, otherwise known as spinal stenosis, is visible in the image data 100. Spinal cord compressions may be caused by arthritis, bulging discs, a thickening of the ligaments in the back, injury, or other causes, and often result in patient pain. The at least one compression 106 may be alleviated by, for example, performing a decompression procedure to remove bone or disc material causing the compression.

Each of these features in the spine region 102, including the spinal cord 104, the compression 106, the at least one nerve exit 108, and the plurality of vertebrae 110, may be identified using the image data 100. Identification of the spinal cord 104, the at least one nerve exit 108, and the plurality of vertebrae 110 may be accomplished using feature-based identification. By way of example, feature-based identification may comprise pre-processing the image data 100 by applying one or more filters or other algorithms thereto. The pre-processing may comprise cleaning and/or aligning the image data 100, and/or conducting intensity mapping of the image data 100. The feature-based identification may further comprise applying one or more feature detection algorithms to the image data 100. These algorithms may be used to identify edges, corners or points of interest, blobs or regions of interest, ridges, and/or other defining elements in the image data 100. Identification of these elements may comprise comparing an intensity or other characteristic of one pixel in the image data 100 to the intensity or other corresponding characteristic of one or more adjacent pixels in the image data 100. Pixels having a local maximum or minimum value for intensity or another characteristic may thus be identified, and a determination can be made as to whether such pixels representing a defining element. Other methods of detecting defining elements in an image may also be used.

Once the defining elements of the image data 100 are identified, one or more algorithms may be used to associate or classify a given defining element or group of defining elements with an anatomical feature. Such algorithms may compare the defining element or group of defining elements to one or more predetermined defining elements of a known anatomical feature, and may correlate the defining element or group of defining elements with the known anatomical feature when the comparison determines or calculates a degree of similarity that surpasses a predetermined threshold. In this manner, the vertebrae, spinal cord, nerve exits, and/or other anatomical features may be identified in the image data 100.

To detect the at least one compression 106, a cross-section of the spinal cord 104 (identified as described above), such as the cross-sections shown in FIGS. 1 and 2A, may be generated. Gradient analysis may then be used to identify the edges of the spinal cord 104. Once the edges of the spinal cord 104 have been identified, a distance between the edges may be measured at a plurality of locations along the length of the spinal cord 104 to yield a set of local spinal cord widths. The spinal cord width as measured at any given location may then be compared to the spinal cord width as measured at one or more adjacent locations. A rapid and/or unusual change in spinal cord width at a given spinal location or subset of spinal locations indicates the presence of a compression 106. In some embodiments, the compression 106 may be identified by identifying one or more spinal cord widths along the length of the spinal cord 104 that are below an average spinal cord width of the spinal cord 104 by a predetermined amount, and/or that are lower than a predetermined value.

Various aspects of a decompression procedure may be determined based on the image data 100, as will be discussed below, once spinal stenosis has been detected in the image data 100.

Figure 3:
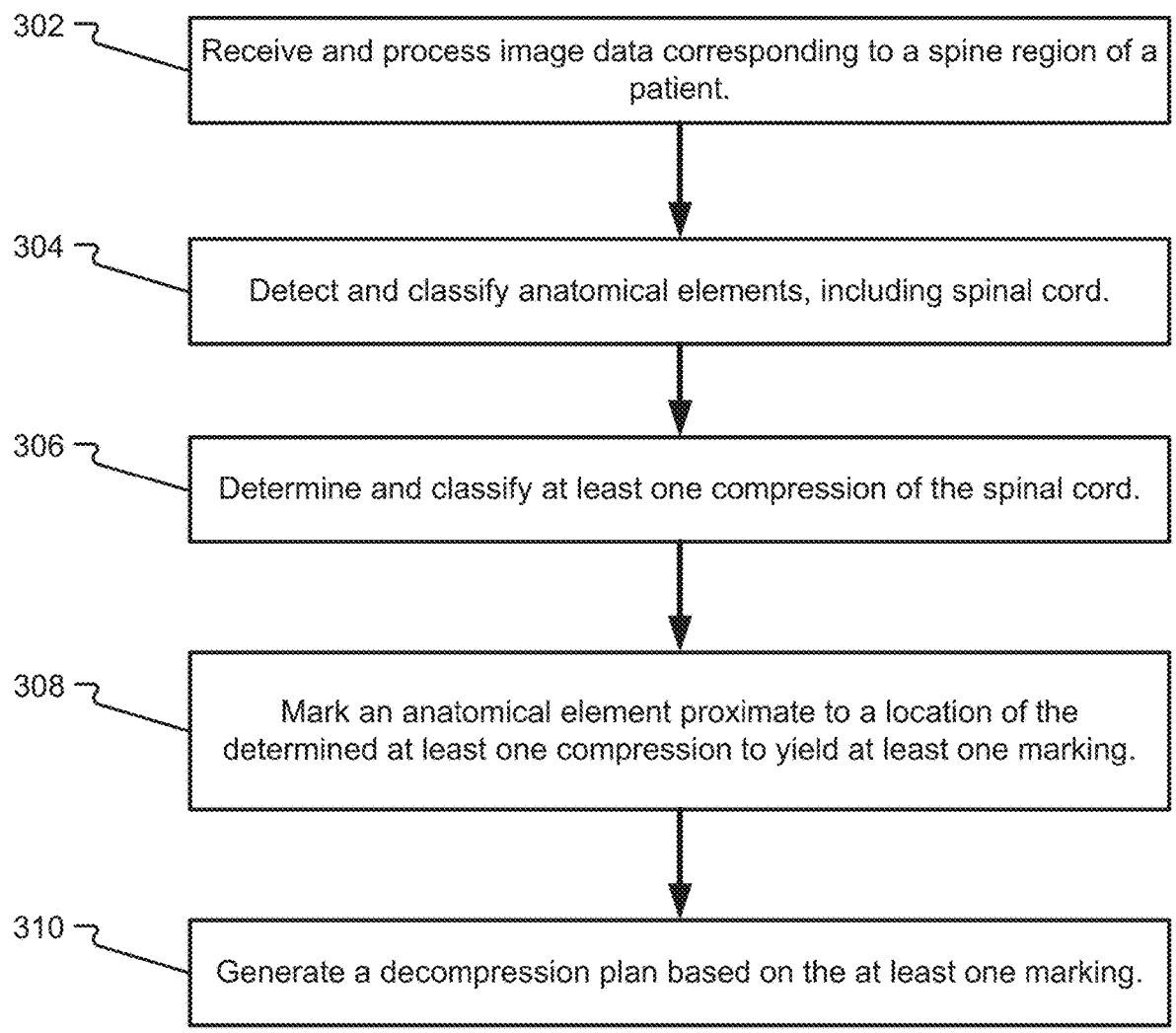
FIG. 3 is a flowchart of a method according to at least one embodiment of the present disclosure.

Turning to FIG. 3, a conceptual flow diagram illustrates a method 300 for detection of spinal stenosis in image data 100. The method 300 may be carried, for example, by a processor executing instructions stored in a memory operatively connected to the processor and configured to cause the processor to carry out the steps 302 through 310 of the method 300.

In the method 300, image data 100 corresponding to a spine region 102 of a patient may be received in step 302, and any needed pre-processing of the image data 100 may be conducted. Such pre-processing may be the same as or similar to the pre-processing described above.

The image data 100 may be received, for example, by a processor executing instructions configured to cause the processor to receive the image data 100. The image data 100 may be provided by a user or may be obtained in real-time, e.g. directly from a device performing an MRI scan or a CT scan, or otherwise scanning a 3D image of a spinal region of a patient. The image data 100 may be received from a tangible electronic storage medium. The image data 100 may be received via a wired or wireless connection. The image data 100 may be received from the Internet, another wide area network, a local area network, or any other network. The image data 100 may be required to have at least a minimum required resolution, or to otherwise meet minimum standards and/or parameters, to ensure that the remaining steps of the method 300 can be completed using the image data 100.

In step 304, a spinal cord 104 and/or other anatomical elements may be identified in the image data 100. Such identification may be performed automatically using, for example, feature-based identification as described above. In some embodiments, the vertebrae locations may be determined based on the unique form of the spine in a 3D volume, e.g., by detecting a unique pattern that repeats itself along a prolonged line with anatomical distinct features, e.g. size, form, volume, etc. Once the vertebrae locations are determined, a spinal cord location may be determined. Such determination of the spinal cord location may be based on the unique features of continuity and general location (including common pathologies) within the spine vertebrae. Nerve exit locations may be determined in the same way. In some examples, individual bony anatomy and intervertebral discs may be detected in the image data 100.

Further, machine learning, deep learning, or artificial intelligence may be used to identify the spinal cord 104 and/or other anatomical elements in the image data 100. For example, a machine learning engine may be trained using historical data and/or training images of a plurality of spine regions in which relevant features have already been identified (e.g., manually). The machine learning engine may utilize the historical data and/or training images to identify patterns, correlations, and/or other relationships that may be used to identify features of interest. Upon receipt of the image data 100, the machine learning engine may apply one or more algorithms reflecting the identified patterns, correlations, and/or other relationships to the image data 100 to yield identified features of interest (including a spinal cord 104).

In some embodiments, a processor or other computing device or system may compare the image data 100 to an atlas of spinal anatomy, and identify one or more anatomical elements in the image data 100 based on the results of the comparison.

In step 306, at least one compression 106 of the spinal cord 104 may be determined or identified. In some examples, determining the at least one compression 106 of the spinal cord 104 may include comparing a first characteristic in the image data 100 with a second characteristic in the image data 100. For example, a width of the spinal cord at a first location may be compared with a width of the spinal cord at a second location adjacent or near the first location. In yet another example, a gradient or other characteristic corresponding to a side of the spinal cord at a first location may be compared with a gradient or other characteristic corresponding to the same side of the spinal cord at a second location near the first location. The comparison may be or comprise a comparison of the magnitude of the gradients being compared, and/or of the relative position of the gradients being compared. In other examples, determining the at least one compression 106 of the spinal cord 104 may include comparing a first characteristic in the image data 100 with a predetermined threshold. In some examples, the predetermined threshold may be based on a historical characteristic of at least one historical patient, or of a population. In other examples, the predetermined threshold may be set by a user, e.g., a physician or surgeon. In still other examples, the predetermined threshold may be calculated based on the image data 100. For example, a width of the spinal cord at a given location may be compared to an average width of the spinal cord across all measured locations of the spinal cord. In still other examples, a compression 106 may be determined by mapping the image data 100 regarding the spinal cord 104 to a large-scale anatomical atlas, by comparing the results of measurements of the previously identified anatomical elements, and using one or more thresholds to determine whether a compression 106 exists. Machine learning, deep learning, or artificial intelligence may be used to determine the at least one compression 106.

An anatomical element proximate to a location of the determined at least one compression 106 may be marked to yield at least one marking in step 308. The at least one anatomical element may be, for example, a vertebra 110, a portion of a vertebra 110, such as a lamina or a foraminal wall, or a disc 112. In some embodiments, the at least one marking comprises a visual indicator, and may visually indicate to a surgeon a location or characteristic of the at least one compression 106, or a location or characteristic of a feature causing the at least one compression 106. In other embodiments, the at least one marking may not comprise a visual indicator, but rather may be intended only to ensure that a processor or other computing device tracks the location of the at least one compression 106 (and/or of an anatomical element causing or otherwise related to the at least one compression 106) and generates an appropriate decompression plan. Whether visual or not, the at least one marking can also include additional information about the at least one compression 106, such as, but not limited to, type, size, volume, severity or the like. Machine learning, deep learning, or artificial intelligence may be used to automatically mark the anatomical element.

In step 310, a decompression plan may be generated based at least in part on the at least one marking. In some embodiments, generation of the decompression plan includes creating a baseline of potential solutions for decompression of the identified compression. The decompression plan may include determining whether a laminectomy, laminotomy, foraminotomy, or other standard procedure will relieve the compression, and may further comprise information about standard cut types and/or designated cuts needed or recommended for carrying out an identified procedure.

For example, generation of the decompression plan may comprise virtually and automatically conducting, with a processor, one or more of a discectomy, a laminotomy, a laminectomy, a foraminotomy, or another procedure, and evaluating, for each procedure, whether the procedure enables the spinal cord 104 to return to a decompressed state. In some embodiments, a score may be calculated for each potential decompression plan that is conducted virtually and automatically, and the resulting set of scores may be used to identify a preferred or recommended decompression plan. The score may be based on, for example, one or more of a likelihood of correcting the compression, a likelihood of inadvertently causing collateral damage during the decompression, an ease of carrying out the decompression, and/or an amount of bone and/or soft tissue removed by the compression (both in the approach to the compression and in the decompression itself).

Also as part of the generation of the decompression plan in some embodiments, a visualization of the identified compression, the aforementioned procedures, and/or a predicted appearance of the spine region (or a portion thereof) after the decompression plan has been performed may be generated. The visualization may be or comprise one or more images and/or one or more videos. The visualization may show a predicted change in the spine region (or a portion thereof, e.g., the portion in which the identified compression is located) as the decompression plan is being carried out, and/or may show a predicted change in the spine region (or a portion thereof, e.g., the portion in which the identified compression is located) after the decompression plan has been performed. The processor may cause the visualization to be displayed on a display (e.g., a monitor, a screen, etc.). The visualization may be evaluated automatically by the processor, or manually by a surgeon or other user for likelihood of success.

Once a procedure is determined to likely be successful (or at least relatively more successful than another procedure) based on the evaluation of the virtual procedure and/or evaluation of the visualization of the virtual procedure, the procedure in question may be selected and recommended to the surgeon or other user. Alternatively, each of a plurality of procedures may first be evaluated, after which one of the plurality of procedures yielding the highest likelihood or probability of success may be selected and recommended to a surgeon or other user. The recommendation may comprise instructions for carrying out the procedure in a suggested or recommended manner in addition to the identification of the procedure.

Generation of the decompression plan may alternatively comprise the use of machine learning, deep learning, or artificial intelligence to determine, based on inputs such as the type and location of an identified compression, a suggested decompression solution for the current patient. The decompression solution may be, for example, the solution that has the highest chance of yielding a desirable outcome, or the least chance of yielding an undesirable outcome. The machine learning system, algorithm, or engine may utilize historical data regarding compressions, historical decompression cuts used to relieve such compressions, and/or historical post-procedure outcomes in making the determination. A recommendation or suggestion based on the determination may comprise a type of procedure as well as instructions for carrying out the procedure.

Generation of the decompression plan may include calculating an amount of bone and/or disc to remove based at least in part on the at least one marking. The decompression plan may identify which portion(s) of one or more vertebrae to remove, which disc(s) to remove (if any), and/or which instruments to use to remove the bone portion(s) and/or disc(s). The calculation may take into account an allowance for bone growth that will not result in a new compression.

Calculation of the amount of bone and/or disc to remove may be automated, which advantageously reduces time needed to generate the decompression plan and further removes guesswork associated with a surgeon's judgment of bone/disc removal.

The decompression plan may also include information or directions for a surgeon and/or surgical robot to identify the bone and/or disc for removal, and may be optimized for the removal of bone or disc material to be performed by a surgeon (whether manually or with the assistance of surgical robotics) or by a robotic surgeon. The decompression plan may also specify or suggest entry points on a surface of a body and/or trajectories for accessing the surgical site with the instruments. Further, calculation of the amount of bone to remove may comprise calculating a minimum number of cuts required to perform the removal. Generation of the decompression plan may include selecting at least one of a full laminectomy, a partial laminectomy, a full laminotomy, a partial laminotomy, a full foraminotomy, and/or a partial foraminotomy.

The decompression plan may comprise a visual element so that a surgeon or other treating physician can easily see the generated plan. For example, the decompression plan may include a graph and/or image(s) illustrating the compression location, entry point location(s), portion(s) of the bone and/or disc to remove, and/or the at least one marking.

The decompression plan may be editable so that a surgeon or other treating physician can make changes to the plan.

The decompression plan may include restrictions on devices or surgical robots to block the devices or surgical robots from leaving a planned section and/or from removing too much of the bone portion(s) and/or disc(s). The decompression plan may also be stored in a computer-readable memory for future reference or use.

The method 300 may be utilized to generate a decompression plan to correct a compression of a spinal nerve exit 108, as well as a compression in a spinal cord 104.

Figure 4:
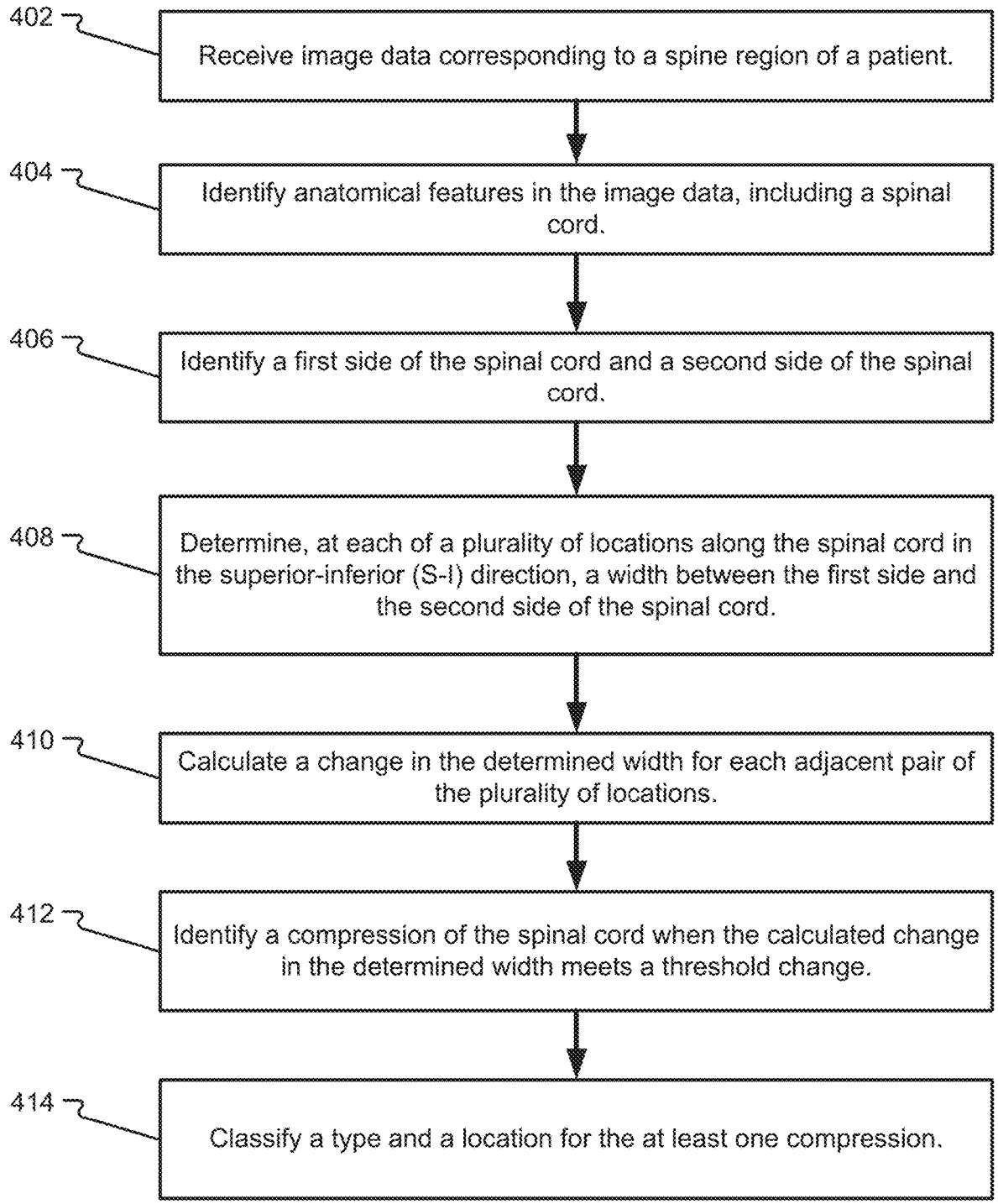
FIG. 4 is a flowchart of a method according to at least one embodiment of the present disclosure.

Turning to FIG. 4, a conceptual flow diagram illustrates a method 400 for detecting spinal stenosis, which will be discussed in conjunction with FIGS. 5A, 5B, 6A, and 6B. As previously described, image data 100 corresponding to a spine region 102 of a patient may be received, for example, by a processor executing instructions configured to cause the processor to receive the image data 100 in step 402.

Figure 5B:
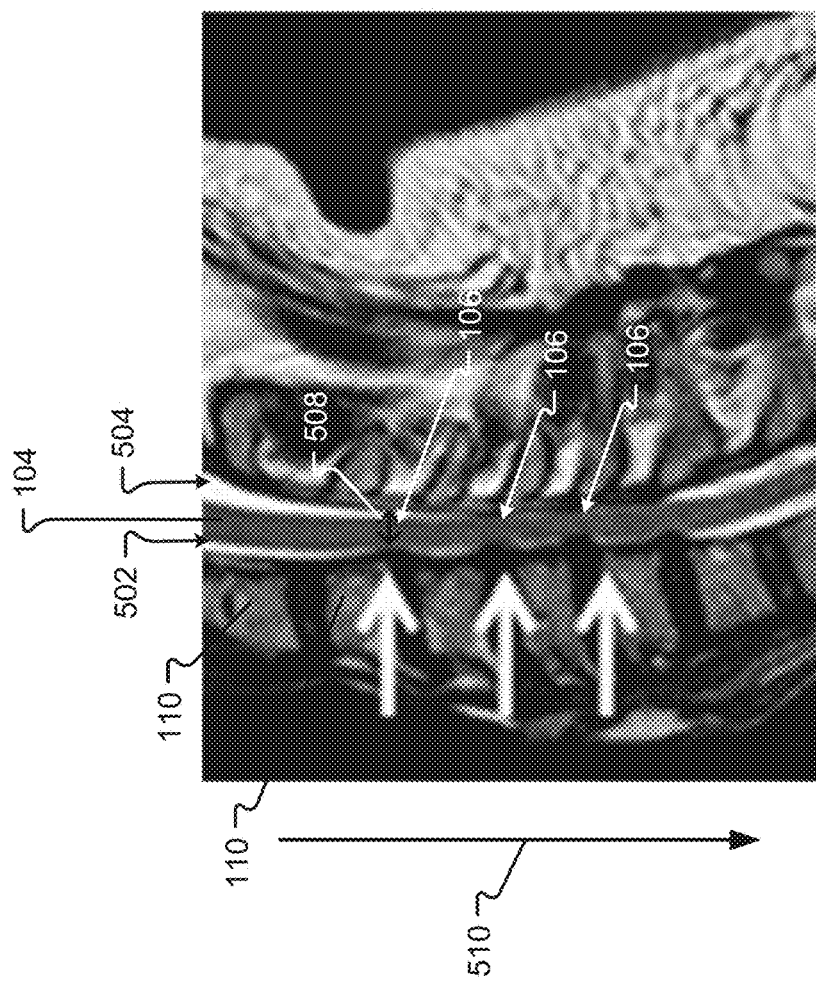
FIG. 5B is a side cross-section view that illustrates a spine region with stenosis.
Figure 5A:
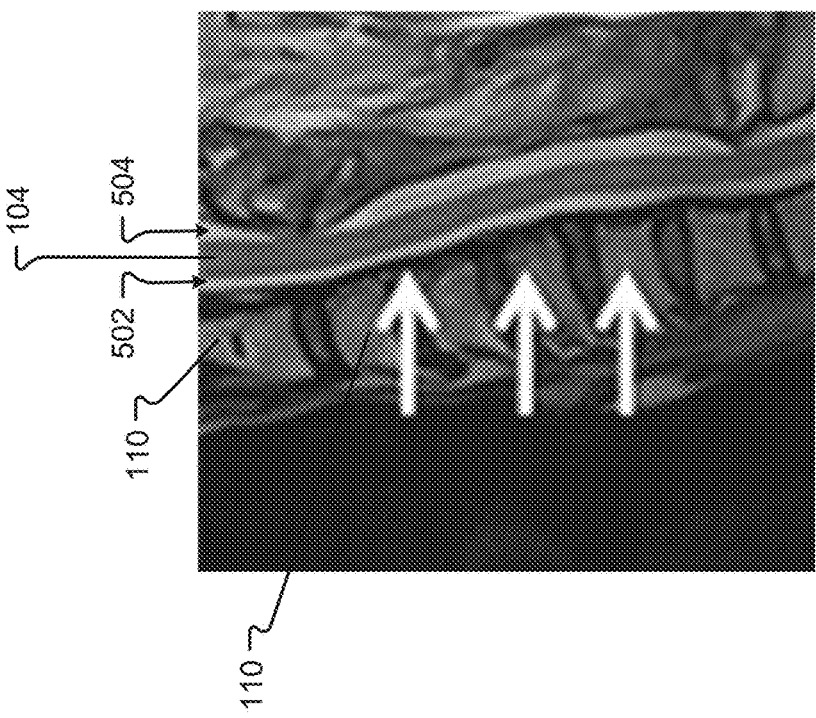
FIG. 5A is a side cross-section view that illustrates a spine region without stenosis.

In step 404, a spinal cord 104, as shown in FIG. 5B, at least one nerve exit 108, and/or other anatomical elements may be identified in the image data 100. In some embodiments, a cross-section of the spinal cord 104 along a plane extending in the superior-inferior (S-I) direction (which direction is shown by arrow 510 in FIG. 5B), as shown in FIGS. 5A and 5B, may be generated from the image data 100.

A first side 502 of the spinal cord 104 and a second side 504 of the spinal cord 104 may be identified in step 406. As shown in FIG. 5A, the first side 502 and the second side 504 are distinguishable from the spinal cord 104 and surrounding anatomical elements. In some examples, the first side 502 and the second side 504 may each correspond to at least one first gradient in the image data 100 and at least one second gradient in the image data 100, respectively. Such identifications of the spinal cord, the at least one nerve exit, the first side, the second side, and/or other anatomical elements may be performed automatically using feature-based identification, or using machine learning, deep learning, and/or artificial intelligence, as previously described above, or in any other manner.

At step 408, a width 508 (shown, for example, in FIGS. 5B and 6B), between the first side 502 and the second side 504 may be determined at a plurality of locations along the spinal cord 104 in the S-I direction. In some examples, the width 508 in each of the plurality of locations may be determined using each of a plurality of gradient graphs 600, as shown in FIG. 6A. The plurality of graphs 600 each show a change in intensity of the image data 100 along a line orthogonal to the spinal cord 104 at one of the plurality of locations. Thus, each of the plurality of graphs 600 corresponds to one of the plurality of locations along the spinal cord 104. In some embodiments, the plurality of graphs 600 may show a change in intensity of the image data 100 along a line orthogonal to the cross-section of a nerve exit 108 at each of a plurality of locations. The plurality of graphs 600 may be generated, for example, based on gradients in the grey-level contrast (which shows the contrast between nerves and bony anatomy) of the image data 100. The plurality of graphs 600 may be generated by a processor executing instructions configured to cause the processor to generate the plurality of graphs 600.

The plurality of graphs 600 provides a simple visual representation of the spinal cord 104 and surrounding area at given locations, and provides discrete data for computer-based analysis. In some embodiments the plurality of graphs 600 may be displayed on a display of, for example, a computing device, for viewing by a user, while in other embodiments the plurality of graphs 600 may not be displayed.

Figure 6B:
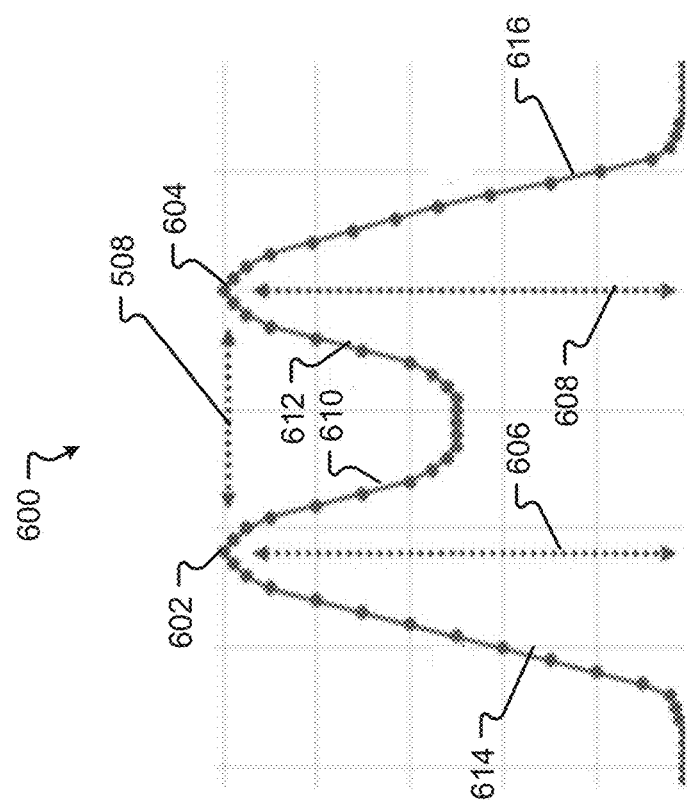
FIG. 6B is a single one of the plurality of graphs shown in FIG. 6A.
Figure 6A:
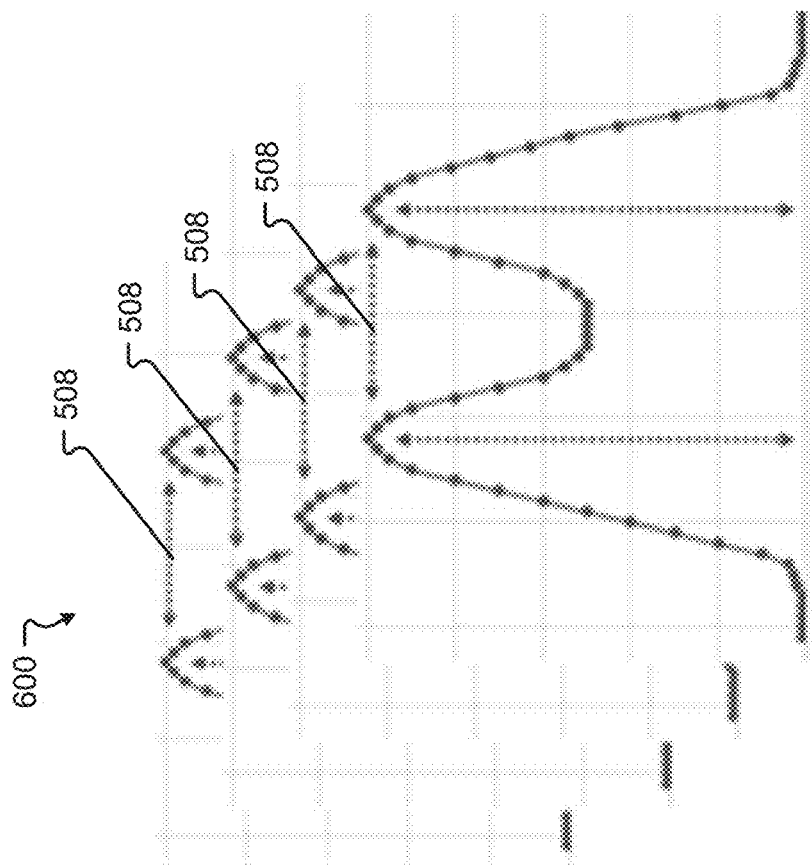
FIG. 6A shows a plurality of graphs corresponding to a plurality of adjacent locations along on a spine region.

Each graph may depict a first peak 602 and a second peak 604, illustrated in FIG. 6B. The first peak 602 may have a height 606 corresponding to a first maximum intensity of the image data 100 (which corresponds or is assumed to correspond to a left edge of the spinal cord 104), with gradients 610 and 614 extending on either side of the first peak 602. The second peak 604 may have a height 608 corresponding to a second maximum intensity of the image data 100 (which corresponds or is assumed to correspond to a right edge of the spinal cord 104), with gradients 612 and 616 extending on either side of the second peak 604. A distance between the first peak 602 and the second peak 604 therefore corresponds or is assumed to correspond to the width 508 of the spinal cord 104. The slopes of the gradients 610, 612, 614, and 616 of the graphs 600 represent the rate of change in the intensity of the image data 100.

At step 410, a change in the determined width 508 for each adjacent pair of the plurality of locations may be calculated. The change in the determined width 508 may be based on a comparison of pairs of the plurality of graphs 600 corresponding to adjacent pairs of the plurality of locations. For example, the width 508 in one graph 600 corresponding to a first location on the spinal cord 104 may be compared to the width 508 in a second graph 600 corresponding to a second location on the spinal cord 104, the second location adjacent to the first location. The change in the width 508 from one location to an adjacent location may be zero or minimal, or the change may be non-zero and non-minimal. The comparison may be performed automatically or manually. In some embodiments, a change in width across more than two graphs 600 (each of the graphs 600 representing a location adjacent to at least one other of the more than two graphs 600) may be calculated.

At least one compression 106 of the spinal cord 104 may be identified in step 412 when the calculated change in the determined width 508 at or near a given location meets a threshold change. The threshold change may be predetermined or dynamically calculated. The threshold change may be based on, for example, a comparison of historical spinal image data of patients without spinal stenosis and historical image data of patients with spinal stenosis. Such data may be provided as training data to a machine learning, deep learning, and/or artificial intelligence system or engine, which may be used to identify an absolute or relative amount of change in the width of a spinal cord that corresponds to stenosis. Thus, a decrease in spinal cord width of, for example, 0.7 mm or 5% within a particular section of the spinal cord may be normal among patients without stenosis, while a decrease in spinal cord width of, for example, 0.91 mm or 7% within a particular section of the spinal cord may be abnormal or altogether absent among patients without stenosis, yet common in patients with stenosis. Because the maximum, minimum, and average widths of a spinal cord vary from person to person, a relative threshold change value (e.g., a percentage change in width) may be more useful than an absolute threshold change value (e.g., a change in width measured in mm or inches). However, both absolute and relative threshold changes are included within the scope of the present disclosure.

The compression 106 may also be identified using only information about the spinal cord 104 obtained from the image data 100. Such information may include, for example, one or more inconsistencies and/or non-minimal changes in the measured distance 508 within pairs or sets of the plurality of graphs 600 corresponding to adjacent pairs or groups of adjacent pairs of the plurality of locations. A compression 106 may also be identified based on changes in the magnitude of the peaks 602 and 604 within pairs or sets of graphs 600 corresponding to adjacent pairs or groups of adjacent pairs of the plurality of locations in the image data 100.

At step 414, the at least one compression 106 is classified by type and location. The classification may also involve identifying bony anatomy sections (such as vertebrae and/or different parts of vertebrae, e.g., the lamina, spinous process, facets, pedicles, or the like) and/or discs adjacent to the compression area. Such classification and/or identification may be performed automatically using feature-based identification, as described above. In other embodiments, machine learning, deep learning, or artificial intelligence may be used to automatically classify the at least one compression 106 and/or identify nearby bony anatomy/disc sections. In some examples, neural networks may apply algorithms based on historical or predetermined anatomical annotations and/or historical decompression surgery results to classify the at least one compression 106 and/or identify nearby bony anatomy/disc sections.

In some examples, the image data 100 may be annotated based on the classification of the at least one compression 106. For example, the bony anatomy (whether vertebrae, parts of vertebrae, or both) and/or discs adjacent to the compression area may be annotated. The annotation may include the classification and information about the compression and/or the bony anatomy/disc (e.g., type, size, volume, area, or the like). In other examples, an anatomical element proximate to a location of the determined at least one compression 106 may be marked to yield at least one marking. As previously described, the at least one marking may comprise a visual indicator or may include information for a processor or other computing device to process before, during, or after generation or execution of the decompression plan. The at least one marking may include the information provided by the annotation. In some embodiments, such classification and/or at least one marking may be used to calculate the amount of bone to remove during the decompression procedure. In other examples, the classification may be used to determine whether to perform a laminectomy, a partial laminectomy, a full laminotomy, a partial laminotomy, a full foraminotomy, or a partial foraminotomy to provide relief to the compression. IN still other examples, the classification may be used to provide instructions for performing a laminectomy, a partial laminectomy, a full laminotomy, a partial laminotomy, a full foraminotomy, or a partial foraminotomy to provide relief to the compression. Such annotations and/or at least one marking may be useful to surgeons and/or may be used in generation of the decompression plan, as previously described above.

Figure 7:
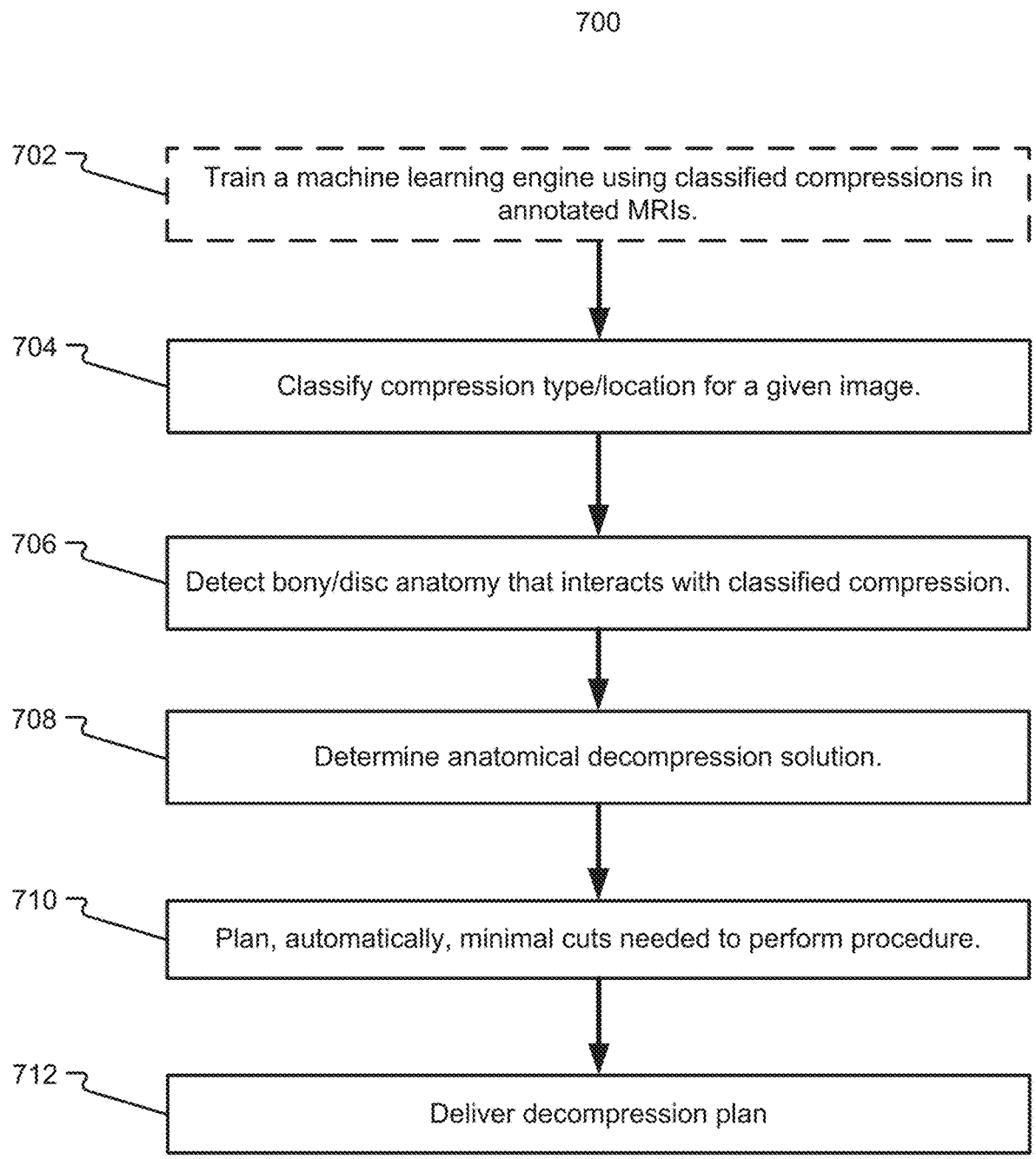
FIG. 7 is a flowchart of a method according to at least one embodiment of the present disclosure.

Turning now to FIG. 7, a method 700 of preparing a decompression plan may comprise, in step 702, training a machine learning engine using classified compressions in manually annotated Mills or other images. Thus, the machine learning engine may correlate documented clinical outcomes of procedures (e.g., whether a procedure has relieved the correct compression) and related information (e.g., information about patient characteristics, stenosis characteristics, type of procedure performed, a manner in which the procedure was performed, and so forth), combined with the annotations in the MM or other image (reflecting, e.g., information about the spinal cord 104 and/or other anatomical elements in the image) with annotated compression classifications. Alternatively, the machine learning engine may identify or determine one or more thresholds to use for classifying compressions and/or evaluating which procedures are most likely to be successful in correcting a compression based on information about the compression.

The step 702 need only be completed once, although it may be repeated as desired to further improve the machine learning engine (e.g., by providing additional training data to the machine learning engine). In embodiments that do not use a machine learning engine to determine an anatomical decompression solution, the step 702 may be omitted.

The method 700 may comprises, in step 704, classifying a type (based, e.g., on the cause of the compression, such as a bulging disc or a displaced vertebra) and location (e.g., where along the spine) of a compression 106 identified in an MM or other image.

The method 700 also comprises, in step 706, detecting one or more pieces or portions of bony anatomy and/or discs that interact with and/or cause the classified compression 106. The detecting may be based on a previously made marking (e.g., a marking made in a manner described above), or the detecting may comprise marking the bony anatomy and/or disc(s) adjacent to or within a certain distance of the compression 106, in the same or a similar manner as described elsewhere herein.

The method 700 may further comprise, in step 708, determining an anatomical decompression solution. The anatomical decompression solution may be determined using, for example, the trained machine learning engine, to which may be input information about the compression 106 presently in need of correction. In other embodiments, the anatomical decompression solution may be determined by virtually and automatically conducting, with a processor, one or more of a discectomy, a laminotomy, a laminectomy, a foraminotomy, or another decompression procedure, and evaluating, for each procedure, whether the procedure enables the spinal cord 104 to return to a decompressed state. Once a procedure is determined to likely be successful (or at least relatively more successful than another procedure), the procedure in question may be selected and recommended to a surgeon or other user. Alternatively, each of a plurality of procedures may first be evaluated, after which one of the plurality of procedures yielding the highest likelihood or probability of success may be selected and recommended to a surgeon or other user.

The decompression solution may be or include a general approach (e.g., a laminectomy, laminotomy, foraminotomy, discectomy) as well as more specific information, such as on which vertebra(e) or disc(s) to perform the procedure, and how much bone to remove (in the case, e.g., of a laminotomy or foraminotomy).

The method 700 may further comprise, in step 710, automatically planning a minimal number of cuts needed to perform the determined decompression solution. As with the determining an automatic decompression solution described above, the automatically planning a minimal number of cuts needed to perform the determined decompression solution may be completed using, for example, a trained machine learning engine, and may be based at least in part on historical procedure information, historical outcome information, and/or information about or corresponding to the compression 106 presently in need of correction. Alternatively, the automatically planning the minimal number of cuts needed to perform the determined decompression solution may be completed based on one or more automatic and virtual simulations of the recommended procedure (which may, for example, evaluate projected outcomes based on different numbers of cuts, or may simply determine how many cuts are required for the procedure in question).

The method 700 may further comprise, in step 712, delivering a decompression plan. The decompression plan may comprise, for example, the determined anatomical decompression solution, and/or a plan for the minimal cuts needed to perform the determined anatomical decompression solution. The plan may be delivered via a screen or other user interface, and/or may be delivered as a file transmitted electronically (whether via a physical removable storage medium, or via a wired or wireless connection, a local or wide area network, or otherwise). The plan may also be stored for future use and reference. In some embodiments, the plan may be annotated after completion of the planned procedure to include the results of the procedure and/or notes about the performance of the procedure.

Figure 8:
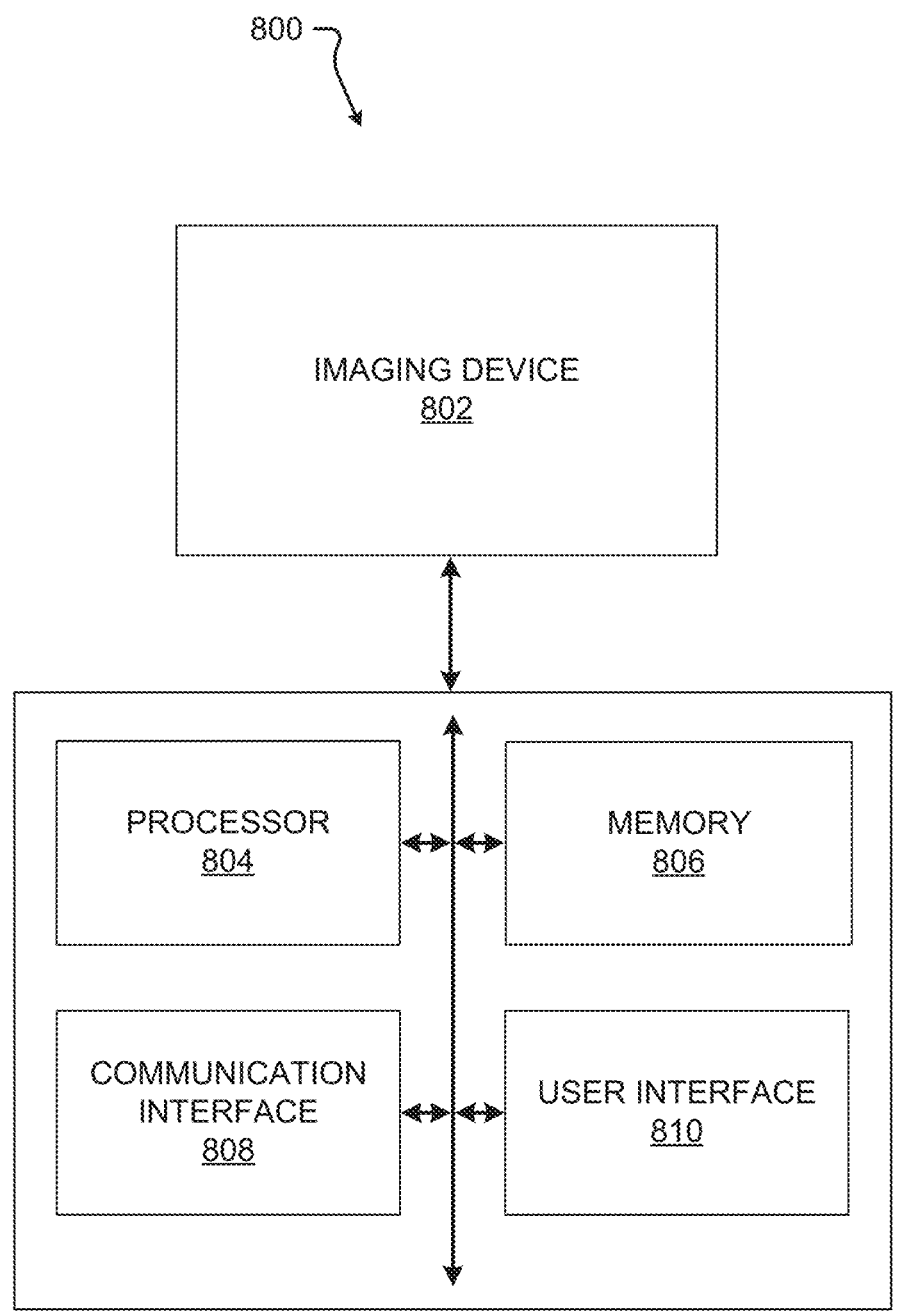
FIG. 8 is a block diagram of a system for detecting spinal stenosis according to at least one embodiment of the present disclosure.

Turning to FIG. 8, a block diagram of a system 800 according to at least one embodiment of the present disclosure is shown. The system 800 may be used to detect spinal stenosis, classify a compression, and/or generate a decompression plan, as described above. The system 800 may comprise an imaging device 802 operable to image an anatomy of a patient (e.g., a spine region) to yield image data (e.g., image data 100 depicting spine region 102 as previously described with respect to FIGS. 1, 2A, 2B, 5A, and 5B). The imaging device 802 may be, but is not limited to, a magnetic resonance imaging (MM) scanner, a CT scanner or other X-ray machine, an ultrasound scanner, or the like. The system may further comprise a processor 804 and a memory 806 storing instructions for execution by the processor 804. Execution of the instructions by the processor 804 may cause the processor 804 to perform any step of any of the methods 300, 400, and/or 700 previously described with respect to FIGS. 3, 4, and 7.

The processor 804 may be an application specific integrated circuit (ASIC), microprocessor, programmable controller, or the like.

The memory 806 may be or comprise RAM, DRAM, SDRAM, or other solid state memory. The instructions stored in the memory 806 may be, or may comprise part of, a machine learning engine. The memory 806 may further store information or data useful for completing any step of any of the methods 300, 400, and/or 700. For example, the memory 806 may store training data for training a machine learning engine; historical patient data; historical compression data; historical decompression plans; historical outcome data; simulation data (e.g., for simulating one or more procedures on a given compression 106); and/or atlas data (e.g., regarding one or more regions of anatomy). The memory 806 may store one or more decompression plans for use by a surgeon or other user in connection with one or more present compressions 106. The memory 806 may also store one or more modifications to such decompression plans, which modifications may have been made a surgeon or other user.

The system 800 may also comprise a communication interface 808. The communication interface 808 may be used for receiving images or other information from an external source, and/or for transmitting decompression plans, images, or other information to an external source. The communication interface 808 may comprise one or more wired interfaces (e.g., a USB port, an ethernet port, a Firewire port) and/or one or more wireless interfaces (configured, for example, to transmit information via one or more wireless communication protocols such as 802.11 a/b/g/n, Bluetooth, NFC, ZigBee, and so forth). In some embodiments, the communication interface may be useful for enabling the system 800 to communicate with one or more other processors or processing engines.

The system 800 may also comprise one or more user interfaces 810. The user interface 810 may be or comprise a keyboard, mouse, trackball, monitor, touchscreen, and/or any other device for receiving information from a user and/or for providing information to a user. The user interface 810 may be used, for example, to display a decompression plan to a surgeon or other user. In some embodiments, the user interface 810 may be useful to allow a surgeon or other user to modify a decompression plan.

Each of the methods 300, 400, and/or 700 may be used in connection with a compression of a spinal cord 104 and/or a nerve exit 108. Any step of any one of the methods 300, 400, and/or 700 may be used in any other one of the methods 300, 400, and/or 700.

Automatic detection of spinal stenosis, generation of a decompression plan, and/or classification of the spinal stenosis reduces time and effort typically required by a surgeon or other practitioner. Further, automatic generation of the decompression plan removes guesswork associated with conventional decompression planning and storage of the decompression plan provides a repository for future reference and use. Such repository can be used to optimize future decompression plans by providing references for generation of decompression plans using machine learning, deep learning, and/or artificial intelligence.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for detecting spinal stenosis comprising:
receiving image data corresponding to a spine region of a patient;
identifying a spinal cord in the image data;
generating, from the image data, a cross-section of the spinal cord along a plane extending in a superior-inferior (S-I) direction;
generating, by a processor, a plurality of graphs, each corresponding to one of a plurality of locations along the spinal cord in the S-I direction, based on a measurement orthogonal to the cross-section of the spinal cord, wherein each of the plurality of graphs depicts a first peak and a second peak, the first peak having a height corresponding to a maximum magnitude of a first gradient corresponding to a first side of the spinal cord, the second peak having a height corresponding to a maximum magnitude of a second gradient corresponding to a second side of the spinal cord;
determining, at each of the plurality of locations along the spinal cord in the S-I direction, a width between the first side and the second side of the spinal cord as a distance between the first peak and the second peak;
calculating, by the processor, a change in the determined width for each adjacent pair of the plurality of locations based on a comparison of the graphs for each adjacent pair of the plurality of locations;
determining at least one compression of the spinal cord when the calculated change in the determined width meets a threshold change; and
classifying a type and a location for each of the at least one compression.

2. The method of claim 1, furthering comprising:
marking an anatomical element proximate to a location of the determined at least one compression to yield at least one marking; and
generating a decompression plan based on the at least one marking.

3. The method of claim 2, wherein generating the decompression plan comprises:
calculating an amount of bone to remove based on the at least one marking.

4. The method of claim 2, wherein generating the decompression plan comprises:
calculating a score for each of a plurality of potential decompression plans.

5. The method of claim 2, wherein generating the decompression plan comprises:
generating a visualization of a predicted appearance of the spine region after the decompression plan has been performed.

6. The method of claim 2, wherein at least one of the steps of identifying the spinal cord in the image data, determining the at least one compression of the spinal cord, and marking the anatomical element use at least one of machine learning, deep learning, and artificial intelligence.

7. The method of claim 2, wherein at least one of identifying the spinal cord in the image data, determining the at least one compression in the spinal cord, and marking the anatomical element use feature-based identification.

8. The method of claim 2, wherein generating the decompression plan includes selecting at least one of a full laminectomy, a partial laminectomy, a full laminotomy, a partial laminotomy, a full foraminotomy, and a partial foraminotomy.

9. The method of claim 2, wherein generating the decompression plan is based at least in part on historical decompression surgery data comprising information regarding a historical patient having a historical characteristic similar to a characteristic of the patient.

10. The method of claim 1, wherein determining the at least one compression of the spinal cord includes comparing a first characteristic in the image data with a second characteristic in the image data to determine the at least one compression.

11. The method of claim 1, wherein determining the at least one compression of the spinal cord includes comparing a characteristic in the image data with a predetermined threshold and determining that the characteristic meets the predetermined threshold.

12. A method for detecting spinal stenosis comprising:
receiving image data corresponding to a spine region;
identifying, in the image data, a spinal cord and at least one nerve exit proximal to the spinal cord;
identifying a first side of the spinal cord and a second side of the spinal cord;
determining, at each of a plurality of locations along the spinal cord in a superior-inferior (S-I) direction, a width between the first side and the second side of the spinal cord by:
generating, from the image data, a cross-section of the spinal cord along a plane extending in the S-I direction; and
generating, by a processor, a plurality of graphs, each corresponding to one of the plurality of locations, based on a measurement orthogonal to the cross-section of the spinal cord, wherein each of the plurality of graphs depicts a first peak and a second peak, the first peak having a height corresponding to a maximum magnitude of a first gradient corresponding to the first side, the second peak having a height corresponding to a maximum magnitude of a second gradient corresponding to the second side, wherein a distance between the first peak and the second peak corresponds to the width;
calculating, by the processor, a change in the determined width for each adjacent pair of the plurality of locations based on a comparison of the graphs for each adjacent pair of the plurality of locations;
identifying at least one compression of the spinal cord when the calculated change in the determined width meets a threshold change; and
classifying a type and a location for each of the at least one compression.

13. The method of claim 12, further comprising displaying the graphs on a display.

14. The method of claim 13, further comprising displaying an image of the spinal cord on the display as reconstructed from the image data.

15. The method of claim 14, wherein the determined at least one compression comprises multiple determined compressions.

16. The method of claim 12, further comprising marking, in the image data, an anatomical element proximate to a location of the determined at least one compression to yield at least one marking.

17. The method of claim 16, further comprising generating a decompression plan based on the at least one marking.

18. A system for detecting spinal stenosis comprising:
an imaging device imaging a spine region to yield image data;
a processor; and
a memory storing instructions for execution by the processor that, when executed, cause the processor to:
receive the image data;
identify a spinal cord in the image data;
generate, from the image data, a cross-section of the spinal cord along a plane extending in a superior-inferior (S-I) direction;
generate a plurality of graphs, each corresponding to one of a plurality of locations along the spinal cord in the S-I direction, based on a measurement orthogonal to the cross-section of the spinal cord, wherein each of the plurality of graphs depicts a first peak and a second peak, the first peak having a height corresponding to a maximum magnitude of a first gradient corresponding to a first side of the spinal cord, the second peak having a height corresponding to a maximum magnitude of a second gradient corresponding to a second side of the spinal cord;
determine, at each of the plurality of locations along the spinal cord in the S-I direction, a width between the first side and the second side of the spinal cord as a distance between the first peak and the second peak;
calculate a change in the determined width for each adjacent pair of the plurality of locations based on a comparison of the graphs for each adjacent pair of the plurality of locations;
determine at least one compression in the spinal cord when the calculated change in the determined width meets a threshold change; and
classifying a type and a location for each of the at least one compression.

19. The system of claim 18, wherein the memory further includes instructions that, when executed, cause the processor to:
mark, in the image data, an anatomical element proximate to a location of the determined at least one compression to yield at least one marking; and
generate a decompression plan based on the at least one marking.

20. The system of claim 19, wherein the memory further includes instructions that, when executed, cause the processor to:
calculate an area for bone removal on the spinal cord based on the at least one marking for the decompression plan.

* * * * *